(12) United States Patent
Zhao et al.

(10) Patent No.: US 8,692,214 B2
(45) Date of Patent: Apr. 8, 2014

(54) CHARGED PARTICLE BEAM INSPECTION METHOD

(75) Inventors: Yan Zhao, San Jose, CA (US); Jack Jau, Los Altos Hills, CA (US)

(73) Assignee: Hermes Microvision, Inc., Hsin-Chu (TW)

( * ) Notice: Subject to any disclaimer, the term of this patent is extended or adjusted under 35 U.S.C. 154(b) by 186 days.

(21) Appl. No.: 12/540,357

(22) Filed: Aug. 12, 2009

(65) Prior Publication Data

US 2011/0036981 A1  Feb. 17, 2011

(51) Int. Cl.
*G21G 5/00* (2006.01)

(52) U.S. Cl.
USPC .............. 250/492.2; 250/492.1; 250/492.22

(58) Field of Classification Search
USPC ........... 250/306, 307, 310, 311, 492.1, 492.2, 250/492.22, 492.3
See application file for complete search history.

(56) References Cited

U.S. PATENT DOCUMENTS 4,902,967 A * 2/1990 Flesner .................... 324/754.22
2008/0302964 A1 * 12/2008 Shinada et al. ............... 250/310

* cited by examiner

*Primary Examiner* — Robert Kim
*Assistant Examiner* — Hanway Chang
(74) *Attorney, Agent, or Firm* — WPAT, PC; Justin King

(57) ABSTRACT

An imaging method and apparatus for forming images of substantially the same area on a sample for defect inspection within the area are disclosed. The disclosed method includes line-scanning the charged particle beam over the area to form a plurality of n*Y scan lines by repeatedly forming a group of n scan lines for Y times. During the formation of each group of n scan lines, an optical beam is, from one line scan to another, selectively illuminated on the area prior to or simultaneously with scanning of the charged particle beam. In addition, during the formation of each group of n scan lines, a condition of illumination of the optical beam selectively changes from one line scan to another. The conditions at which individual n scan lines are formed are repeated for the formation of all Y groups of scan lines.

19 Claims, 12 Drawing Sheets

US 8,692,214 B2

CHARGED PARTICLE BEAM INSPECTION METHOD

FIELD OF THE INVENTION

The present invention generally relates to charged particle beam imaging, and more particularly, to a method for forming a plurality of images of substantially the same area on a sample for defect inspection within the area.

BACKGROUND OF THE INVENTION

In the manufacture of semiconductor devices, patterned substrates are inspected for defects so that the production of acceptable devices can be achieved. Inspection of a patterned substrate can be carried out through various technologies, one of which is charged particle beam inspection. A common example of charged particle beam inspection is electron beam (EB) inspection.

EB inspection is performed by scanning an electron beam over surface patterns of devices formed on a substrate, and collecting the secondary electrons emanated from the surface patterns of scanned devices as inspection signals. The signals are processed and represented in grey levels to produce images of surface patterns of the scanned devices.

The patterned surface contains pattern features which either form the electrical devices or direct/indirect electrical connect to the buried devices. The obtained image shown in grey level contrast represents the difference in electrical charging voltages associated with the devices, connections, as well as the materials. The image is thus also known as a voltage contrast (VC) image. Abnormal grey levels, or abnormal VCs, are detected to identify defective devices or connections. For example, if a bright grey level shows up where a darker grey level should have been observed, it is deemed there exists a bright voltage contrast (BVC) defect. On the other hand, if a dark grey level shows up where a brighter grey level should have been observed, it is deemed there exists a dark voltage contrast (DVC) defect.

When the electron beam is scanned over the surface pattern of a device, charging may be induced and accumulate on the device. The resulting charging can be negative or positive, depending on the electron beam conditions (landing energy, beam current, etc.) used, as well as surface pattern materials in exposure to electron beam scanning. In this specification, for a given surface layer of a device, an electron beam condition leading to accumulation of positive charging on the scanned device will be referred to as "positive imaging mode." On the other hand, an electron beam condition leading to accumulation of negative charging on the scanned device will be referred to as "negative imaging mode."

The positive imaging mode or negative imaging mode may lead to different voltage contrast images for a given surface layer of devices. For example, for the positive imaging mode, an open circuit defect may appear relatively dark in the image due to excessive positive charging accumulated if a normal feature is expected to be well grounded, and display a DVC. On the other hand, a short circuit defect may appear relatively bright due to the formed release path of charging if a normal feature is expected to be floated, and display a BVC in the image.

When a semiconductor device is being scanned in a particular imaging mode, its electrical characteristics give rise to a default VC for this device. For instance, metal contact plugs coupled to the same PN junction device may display different VCs in the positive and negative imaging mode, respectively. Taking the positive imaging mode as an example, PN junctions in a normal NMOS device, such as an n-doped region or a plug connected thereto, are typically reverse biased when being scanned in the positive imaging mode, whereas PN junctions in a normal PMOS device, such as a p-doped region or a plug connected thereto, are typically forward biased when being scanned in the positive imaging mode. The biasing condition of these devices affects their VC behaviors, as will be illustrated below.

Referring to the drawings, FIG. 1 is a schematic illustration of MOSFET devices after the process step of metal CMP (Chemical Mechanical Planarization) in the positive imaging mode. FIG. 1A is a schematic illustration of a PMOS transistor being imaged in the positive imaging mode in accordance with the conventional art, and FIG. 1B is a schematic illustration of an NMOS transistor being imaged in the positive imaging mode in accordance with the conventional art.

As shown in FIG. 1A, PMOS transistor 100A comprises a gate plug 101A, a normal P+/N-well plug 102A, an open P+/N-well plug 103A, and a shorted P+/N-well plug 104A. Image 110A illustrates VC behaviors of the respective above components. As the surface is positively charged, normal P+/N-well junction associated to plug 102A is forward biased, thus is in the "ON" state whereby excessive positive charges can be released to N-well via the junction. A normal P+/N-well plug 102A is therefore, to some extent, equivalent to being shorted/leaking to substrate, and appears bright in the voltage contrast image 110A. P+/N-well plug 104A can be shorted to the substrate or gate plug (for example, short/leakage to the substrate is illustrated in the figure as a black strip 107A connecting plug 104A and N-well). Charges on plug 104A can thus be easily released to N-well or substrate regardless of the ON/OFF state of the P+/N-well junction associated to plug 104A. As a result, plug 104A appears brighter in the VC image 110A. Another typical defect is open P+/N-well plug 103A, i.e. the plug does not contact to the buried device as expected. As a result, positive charges on the surface of P+/N-well plug 103A accumulate to a significant level, and deliver a voltage contrast much darker than the normal plugs 102A. The gate plug 101A is equivalent to an open circuit as it is electrically isolated from the substrate (N-well) by a gate dielectric layer 105A, so it appears similar to the open P+/N-well plug 103A. As one can perceive from the image 110A, for inspection of PMOS plugs at a given positive mode imaging condition, it will be easy to identify the defective open P+/N-well plugs 103A from normal P+/N-well plugs 102A with high sensitivity, but difficult or insensitive to identify the P+/N-well short/leakage defects 104A from normal P+/N-well plugs 102A.

Similar inspection of the NMOS transistor is illustrated in FIG. 1B. As shown, NMOS transistor 100B comprises a gate electrode 101B, a normal N+/P-well plug 102B, an open N+/P-well plug 103B, and a shorted N+/P-well plug 104B. Image 110B illustrates the VC behaviors of respective above components. As the surface is positively charged, the N+/P-well junction associated to plug 102B is reverse biased. Therefore, the junction is in the "OFF" state and to some extent equivalent to being an open circuit. As a result, positive charging accumulates on N+/P-well plug 102B, making it appear dark in image 110B. Though the open plug 103B differs from the normal plug 102B in that it is a real open-circuit to the associated buried N+/P-well junction, no significant difference in image contrast is observed between plugs 102B and 103B as they hold the positive charging to a similar level. In real cases, minor junction leakage may exit on the reverse biased N+/P-well junction, thus a normal N+/P-well plug 102B may appear slightly brighter than an open plug 103B as shown in image 110B. Another defect type is junction short or leakage in which the N+/P-well plug 104B may be either leaking a current or directly shorted to the substrate (illustrated in the figure as a black strip 107B connecting plug 104B and P-well). A plug of this defect type releases charges effectively even with its associated junction reverse biased to the OFF state. As a result, shorted plug 104B appears much brighter in image contrast. Gate plug 101B is equivalent to an open circuit as it is electrically isolated from the substrate (P-well) by a gate dielectric layer 105B. Therefore, it appears similar to the open N+/P-well plug 103B in the VC image 110B (darker VC). Hence, it can be perceived from FIG. 1B that for inspection of NMOS plugs at a given positive mode imaging condition, it is difficult or insensitive to identify the defective open N+/P-well plugs 103B from the normal N+/P-well plugs 102B, but it is sensitive to identify the P+/N-well short or leakage defects 104B from normal N+/P-well plugs 102B.

Therefore, a conclusion can be drawn that the positive mode EBI has high sensitivity to capture P+/N-well plug open defects, but suffers low sensitivity in detecting N+/P-well plug open. Different approaches have been proposed to improve the situation, for example, by applying strong extraction field to reversely breakdown the N+/P-well junction, or by charging the sample surface negatively to forward bias the N+/P-well junction (the negative mode scanning). These techniques either suffer high risk of wafer arcing damage as extremely high electrical field is created in the vicinity of wafer, or need at least two separate inspections to detect both the P+/N-well plug open and the N+/P-well plug open, which is time costly.

Another approach to boost the detection sensitivity of, for example, the open N+/P-well plug at the positive imaging mode was proposed by Larry (U.S. Pat. No. 4,902,967). The proposed method uses an optical beam which has energy higher than the band gap to illuminate the device under inspection. Photo-current will be induced while the surface of the device is being scanned, which either induces photocurrent across the N+/P-well junction, or stimulates leakage current across the thin gate oxide. Ground or substrate electrons are able to come up and neutralize the positive charging accumulated on the scanned surface of the device, and the N+/P-well junctions in the scanned device become, to some extent, leaking or shorted regardless of its actual biasing condition (forward or reverse biased) in the normal positive imaging mode. This helps to drain off the accumulated positive charges on the scanned device, especially the reverse biased N+/P-well junctions as illustrated in FIG. 1B.

Referring to FIG. 1C, an NMOS transistor 100C is illustrated being imaged in the positive imaging mode with optical beam illumination in accordance with the conventional art. The NMOS transistor 100C comprises a gate electrode 101C, a normal N+/P-well plug 102C, an open N+/P-well plug 103C, and a shorted N+/P-well plug 104C. Image 110C illustrates the VC behaviors of respective above components. As shown, optical beam illumination stimulates photo-currents. In the presence of the photo-currents, ground or substrate electrons are able to come up and neutralize the positive charging accumulated on the scanned device surface. This helps to drain off the charging accumulated on normal N+/P-well plug 102C. As a result, plug 102C turns bright in image 110C, and thus the contrast between a normal N+/P-well plug 102C and an open N+/P-well plug 103C which appears dark is greatly enhanced whereby detection sensitivity of open N+/P-well plug 103C is improved. It is noted that gate plug 101C also turns relatively brighter as compared to the gate plug 101B of FIG. 1B (inspection without optical illumination). This is due to the stimulated leakage in gate oxide 105C. This phenomenon can be used to separate the normal gate plug and the open gate contact which does not physically land on gate electrode.

One disadvantage of the above approach is that the optical beam will stimulate the normal N+/P-well plug 102C to leak, thus the N+/P-well leakage or short defects such as plug 104C may become difficult to detect. As a result, at least two inspection actions are still needed to accomplish the detection of both the of-interest open and short/leakage defects.

Referring to FIG. 2A, not admitted art, a positive imaging mode VC image is captured, without optical illumination, of a sample containing both NMOS and PMOS transistors. The sample device can be, for example, an SRAM device. Herein, defect 200 A is a P+/N-well open defect displaying a DVC (visually distinguishable), defect 200B is an N+/P-well leakage/short defect displaying a BVC (visually distinguishable), defect 200C is an open N+/P-well plug defect displaying a DVC (less distinguishable). Defect 200D is an open gate contact displaying a DVC (less distinguishable); as shown it is immersed in the normal gate plugs as there are no substantial electrical differences between them. Furthermore, defect 200E is a gate short/leakage defect displaying a BVC (visually distinguishable). No P+/N-well leakage or short defect (BVC) is present in FIG. 2A. In the schematic of FIG. 2B, not admitted art, a positive imaging mode VC image is captured, with optical beam illumination, of the sample device of FIG. 2A. As with the FIG. 2A schematic, the image is captured in positive imaging mode. It can be seen from FIG. 2B that with optical beam illumination all normal N+/P-well plugs turn bright. As a result, the N+/P-well leakage/short defect 200B becomes hidden (less distinguishable) in the normal bright plugs, and the open N+/P-well plug defect 200C stands out (visually distinguishable) as a high contrast dark plug. It is noted that the P+/N-well plug open defect 200A is almost unaffected by the optical beam illumination (visually distinguishable). Also, the optical beam illumination, by stimulating certain level of leakage through the thin gate oxide, turns the gate plug relatively bright. The gate plug defect 200E thus becomes less distinguishable. The open gate plug defect 200D, however, is not affected by this induced gate oxide leakage, thus standing out (visually distinguishable) as a darker plug.

In general processes of semiconductor device manufacture, it is common to see both NMOS and PMOS plugs in a layer from the surface. FIGS. 2A and 2B illustrate complementary images, or complementary imaging approaches, for detecting different types of defects present on a single sample. These complementary approaches may be implemented in the negative imaging mode and applied to other types of devices as well. Since these complementary approaches only require changes in optical beam illumination condition (on/off), there will be a great benefit to combine the above two imaging steps (one with optical beam illumination, the other without) into one imaging sequence for improved throughput without sacrificing the detection sensitivity to different types of defects.

SUMMARY OF THE INVENTION

One embodiment of the present invention discloses an imaging method for forming a plurality of images of substantially the same area on a sample for defect inspection within the area. The images preferably have a size of X*Y pixels with a predefined pixel size p. The images are formed by charged particle beam imaging where a charged particle beam is repeatedly line-scanned over the area with a line-to-line advancement direction perpendicular to the line scan direction.

The disclosed method comprises line-scanning the charged particle beam over the area to form a plurality of n*Y scan lines by repeatedly forming a group of n scan lines for Y times. During the formation of each group of n scan lines, an optical beam is, from one line scan to another, selectively illuminated on the area prior to or simultaneously with scanning of the charged particle beam. In addition, during the formation of each group of n scan lines, a condition of illumination of the optical beam selectively changes from one line scan to another. The conditions at which the individual n scan line is formed are applied to the formation of all groups of n scan lines.

In another embodiment of the present invention, a charged particle beam inspection system is disclosed. The disclosed charged particle beam inspection system comprises a charged particle beam imaging apparatus, an optical beam apparatus, and a defect determination apparatus.

The charged particle beam imaging apparatus is for forming voltage contrast images of a sample by scanning a charged particle beam over the sample surface. The images preferably have a size of X*Y pixels with a predefined pixel size p. The optical beam apparatus is for illuminating an optical beam on the sample.

The defect determination apparatus comprises a control module and an image analysis module, wherein the control module is coupled to the charged particle beam imaging apparatus and the optical beam apparatus for controlling these elements, such that the charged particle beam is line-scanned over the sample surface to form a plurality of n*Y scan lines by repeatedly forming a group of n scan lines for Y times, and during the formation of each group of n scan lines, the optical beam is, from one line scan to another, selectively illuminated on the sample surface prior to or simultaneously with scanning of the charged particle beam, and during the formation of each group of n scan lines, a condition of illumination of the optical beam selectively changes from one line scan to another. The condition at which the individual n scan line is formed may be applied to the formation of all groups of n scan lines. The image analysis module is coupled with the charged particle beam imaging apparatus for receiving and analyzing the voltage contrast images from the charged particle beam imaging apparatus, thereby determining the presence of certain types of defects on the sample.

DESCRIPTION OF THE EXEMPLARY EMBODIMENTS

Although the present invention will be described in accordance with the embodiments shown below, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

As mentioned earlier, when being scanned in a particular mode, a semiconductor device may display a default voltage contrast (VC) which is a result of change in the device's electrical characteristics. Further, this default VC could lead to confusion in identifying the presence of certain types of defects on the semiconductor device. For example, in the positive imaging mode, all PN-junctions of a normal NMOS device are reverse biased; therefore, the normal N+/P-well plugs may appear similar to a defective open plug in the grey level image (e.g. they both display a darker VC). On the other hand, all PN-junctions in a normal PMOS device are forward biased in the positive imaging mode and therefore may appear similar to a junction short/leakage defect in the grey level image (e.g. they both display a brighter VC). Table 1 lists these and other possible cases (in the positive imaging mode).

TABLE 1

| Device | Electrical Characteristic of normal device | Electrical Characteristic of possible defect |
| --- | --- | --- |
| N+/P-well plug | ~open (OFF at reverse bias) | Open; Short, Junction leakage |
| P+/N-well plug | ~short (ON at forward bias) | Open; Short, Junction leakage |
| Gate plug | ~open (isolated from substrate by gate dielectric) | Open; Short/leakage |

It can be seen from Table 1 that the identification of an open defect on an N+/P-well plug may be confused by the normal N+/P-well plugs from the obtained voltage contrast image as both are equivalent to an open circuit, and present in DVC at positive mode. On the other hand, the identification of a short/leakage defect on a P+/N-well plug may be confused by the normal P+/N-well plugs from the obtained voltage contrast images as both plugs are equivalent to short-circuit, and present in BVC at positive mode.

As mentioned earlier, illumination of the optical beam is able to enhance the detection sensitivity of certain types of defects on a specific semiconductor device. Reference is made to Table 2 to indicate a number of general cases:

TABLE 2

| Defect types (on specific plugs) with enhanced detection sensitivity\Optical beam illumination condition | Illumination ON (Condition 1) | Illumination OFF (Condition 2) |
| --- | --- | --- |
| N+/P-well plug | Open | Short/leakage |
| P+/N-well plug | Open | Open |
| Gate plug | Open | Short/leakage |

Figure 1A:
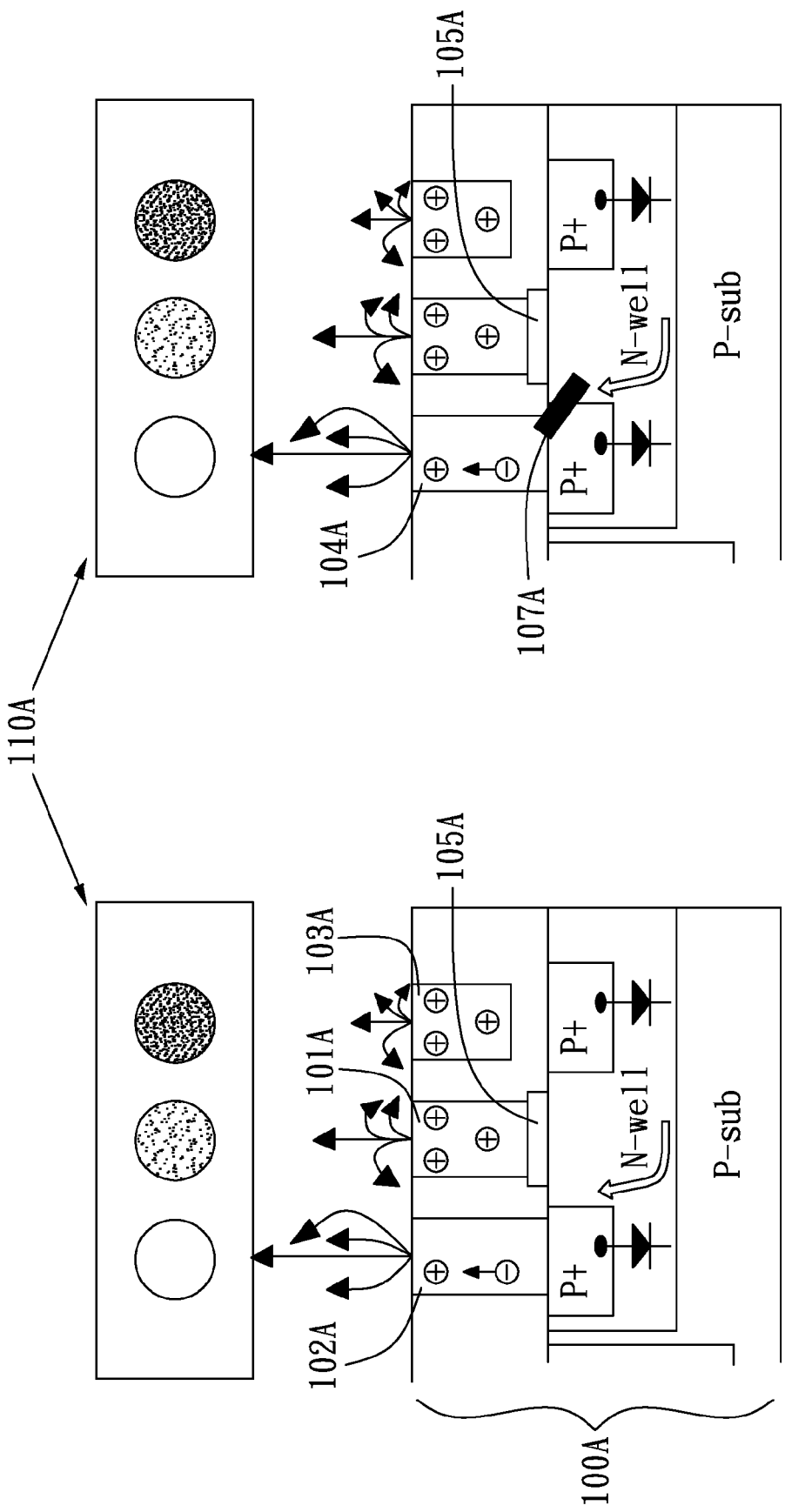
FIG. 1A is a schematic illustration of a PMOS transistor being imaged in the positive imaging mode in accordance with the conventional art.
Figure 1B:
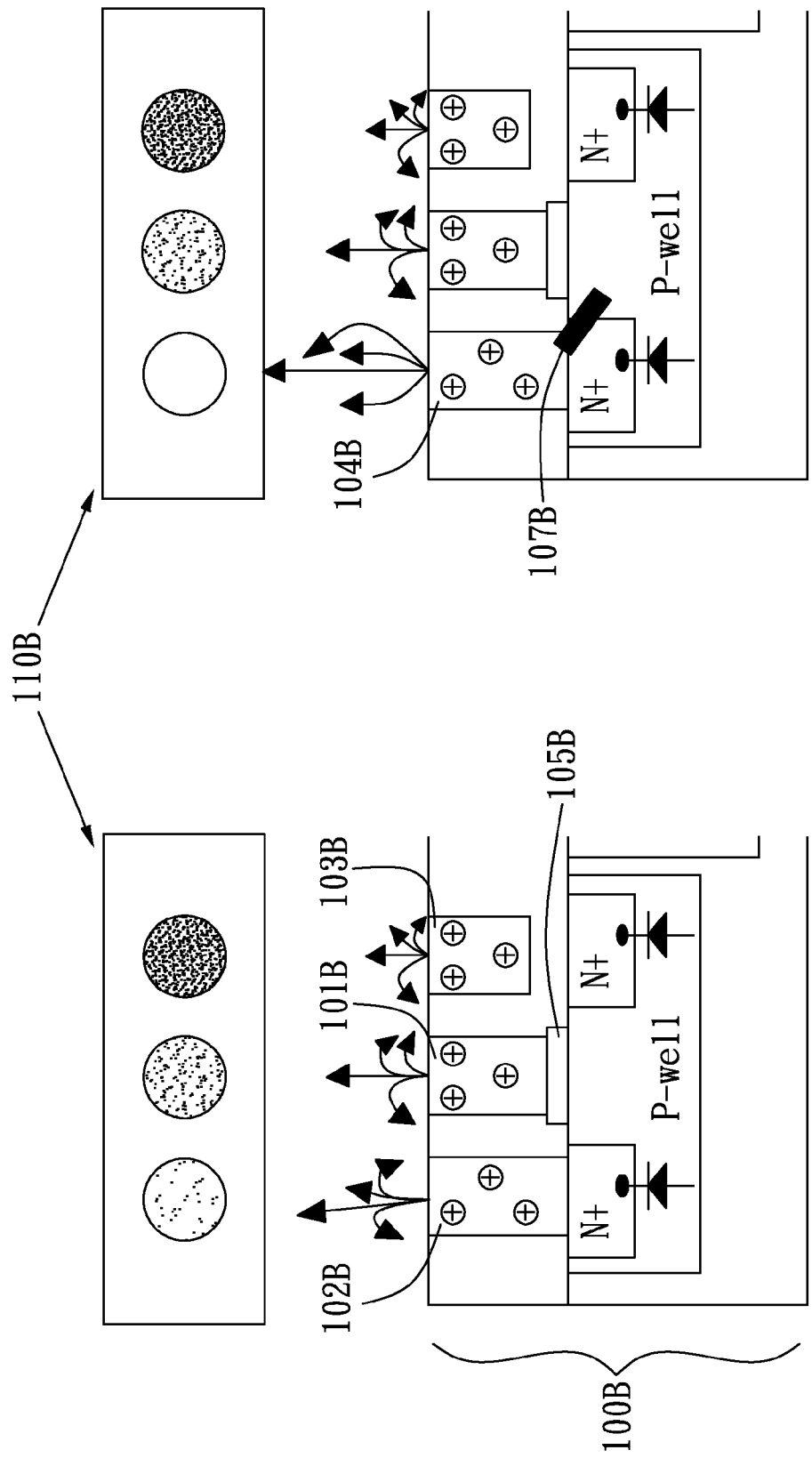
FIG. 1B is a schematic illustration of an NMOS transistor being imaged in the positive imaging mode in accordance with the conventional art.
Figure 1C:
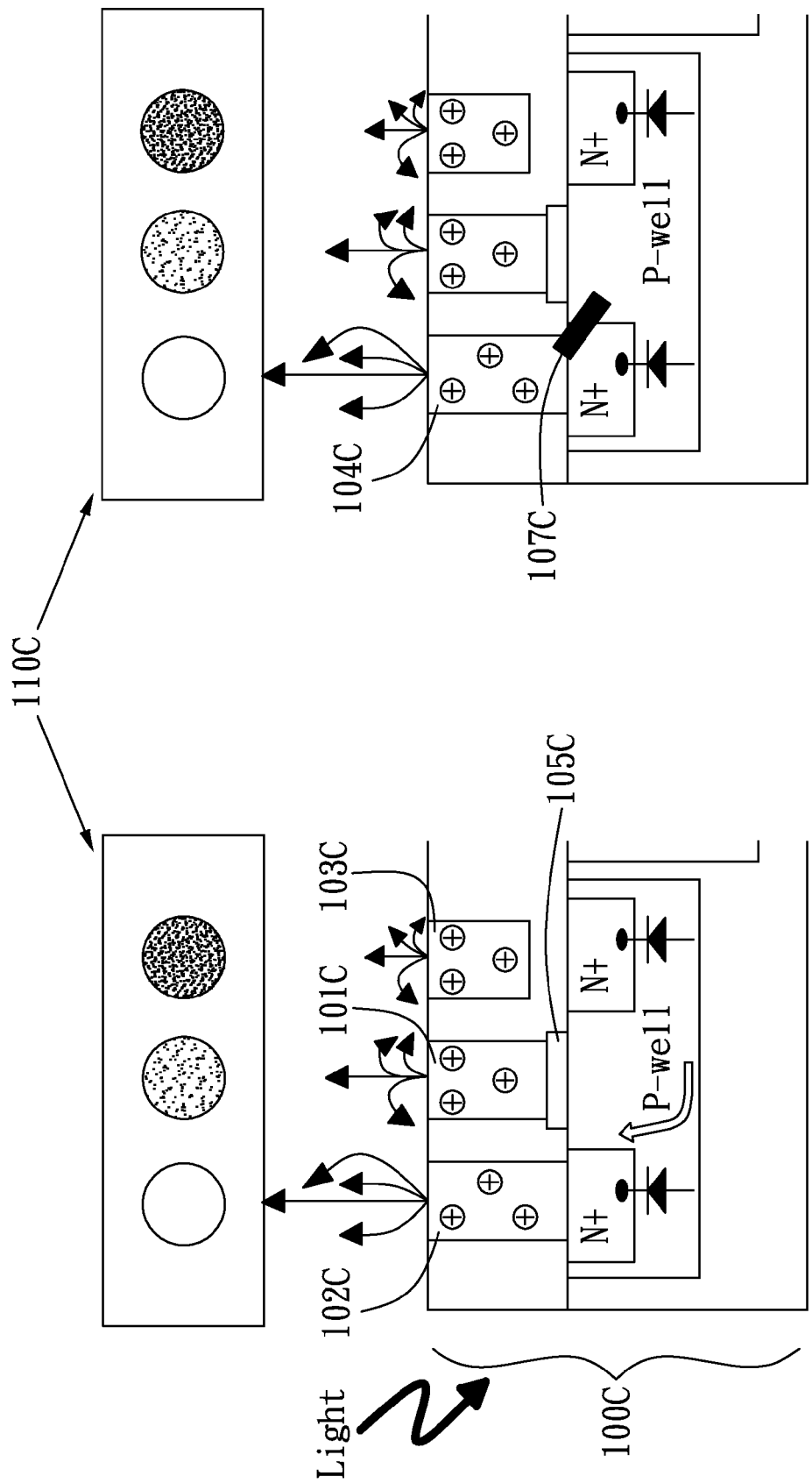
FIG. 1C illustrates an NMOS transistor being imaged in the positive imaging mode with optical beam illumination in accordance with the conventional art.
Figure 2B:
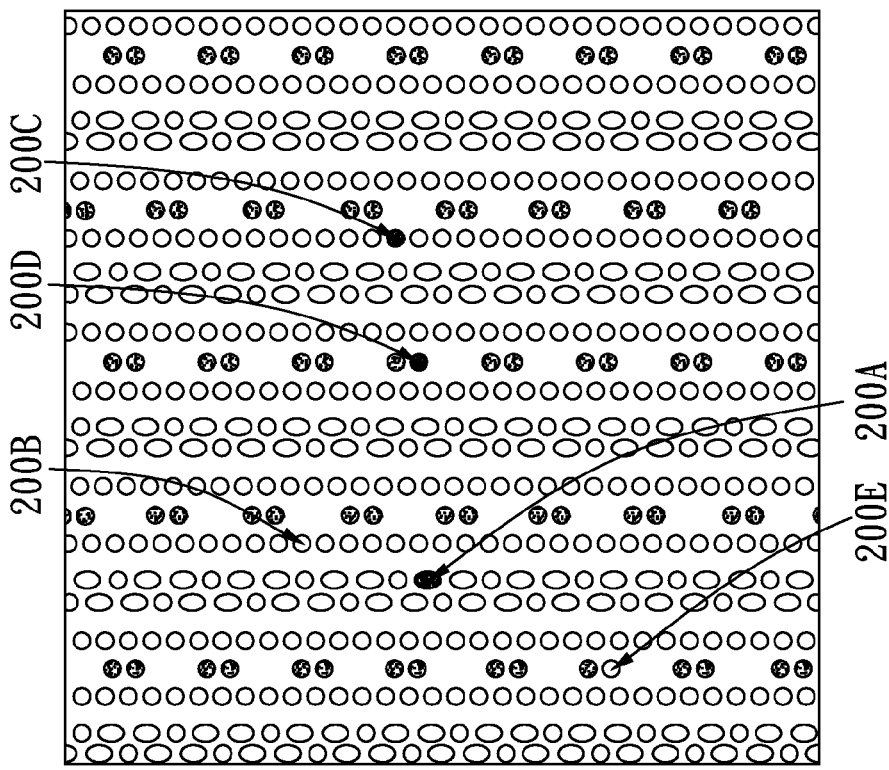
FIG. 2B is a schematic illustration of a positive imaging mode VC image captured with optical beam illumination of the sample device of FIG. 2A.
Figure 2A:
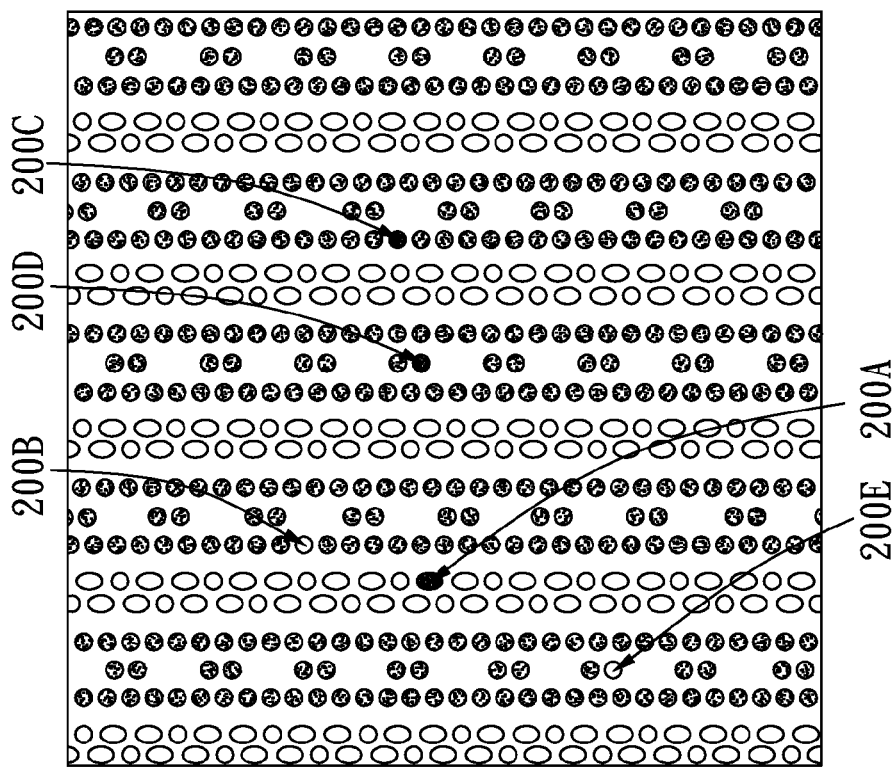
FIG. 2A is a schematic illustration of a positive imaging mode voltage contrast (VC) image captured without optical beam illumination of a sample containing both the NMOS and PMOS transistors.

It can be seen from Table 2, in conjunction with FIGS. 2A and 2B, that the positive imaging mode without optical beam illumination (Condition 2) is sensitive to defects 200A (P+/N-well plug open), 200B (N+/P-well plug short/leakage), and 200E (Gate plug short/leakage), but insensitive to defects 200C (N+/P-well plug open) and 200D (gate plug open). On the other hand, the positive imaging mode with optical beam illumination (Condition 1) is insensitive to defects 200B and 200E, but sensitive to defects 200A, 200C and 200D.

In other words, as an open defect on the P+/N-well plug, defect 200A corresponds to a high detection sensitivity with the optical beam illumination either ON or OFF. As a short or leakage defect on the N+/P-well plug, defect 200B corresponds to a high detection sensitivity with the optical beam illumination OFF. As an open defect on the N+/P-well plug, defect 200C corresponds to a high detection sensitivity with the optical beam illumination ON. Moreover, as an open defect on the gate plug, defect 200D corresponds to a high detection sensitivity with the optical beam illumination ON. Further, as a short or leakage defect on the gate plug, defect 200E corresponds to a high detection sensitivity with the optical beam illumination OFF.

As shown in the examples of FIGS. 2A and 2B, to implement the above approach of optical illumination-assisted inspection, two images can be formed for the same area of interest 20 on a sample, with one of the two images being formed without optical beam illumination and the other formed with optical beam illumination.

Such implementation can be performed in a step-and-scan mode and a continuously moving stage mode. For example, in the step-and-scan mode, two images of substantially the same area of interest may be formed and analyzed to carry out inspection of the area of interest, and then the imaging system, or the sample stage, can move one step to another area of interest on the sample. In the continuously moving stage mode, two images of substantially the same area of interest can be formed by repeating the stage motion, whereby the stage moves forward during one imaging action, then moves back to a designated starting point, and then moves forward again for another imaging action to be performed at substantially the same position on the sample. This algorithm may suffer from (1) the position of scan on the sample being different between the two imaging actions due to mechanical positioning errors; and (2) throughput loss as the stage must move back and forth for the two imaging actions to be performed. Despite these problems, for currently available EBI systems, the continuously moving stage mode imaging will still generally have a higher throughput than the step-and-scan mode imaging method. Therefore, according to an aspect of the invention, it is necessary to integrate the two (or more) complementary imaging approaches into one scan sequence without sacrificing throughput and sensitivity.

In one embodiment, a method of charged particle beam inspection of a semiconductor device is disclosed. The disclosed method scans the sample, such as a patterned surface of a semiconductor device, line by line with a charged particle beam; meanwhile, an optical beam is modulated on/off or to different power levels or selected from different sources of wavelength, in synchronization with the line scans and in a preferred (but not the only) implementation, is kept constant during each line scan. This forms multiple line scans at different optical beam conditions. Formation of such a group of line scans is repeated to complete the whole imaging process.

One objective of the disclosed method is to form one or a plurality of images by a unique scanning sequence over substantially the same area on the sample at different optical beam illumination conditions, which will be referred to as the "imaging condition" hereinafter for simplicity of explanation.

The disclosed method applies to both the continuously moving stage mode and the step-and-scan mode. Conventionally, with either of these two types of modes, a charged particle beam may be repeatedly raster scanned over an area of interest on the sample. Specifically, the charged particle beam is repeatedly line-scanned over the area of interest with a line-to-line advancement direction perpendicular to the line scan direction. In the continuously moving stage mode, the line-to-line advancement is achieved by continuously moving a sample stage whereupon the sample is secured for imaging. In the step-and-scan mode, the line-to-line advancement is achieved by offsetting the charged particle beam by means of, for example, a beam deflection device.

Figure 3A:
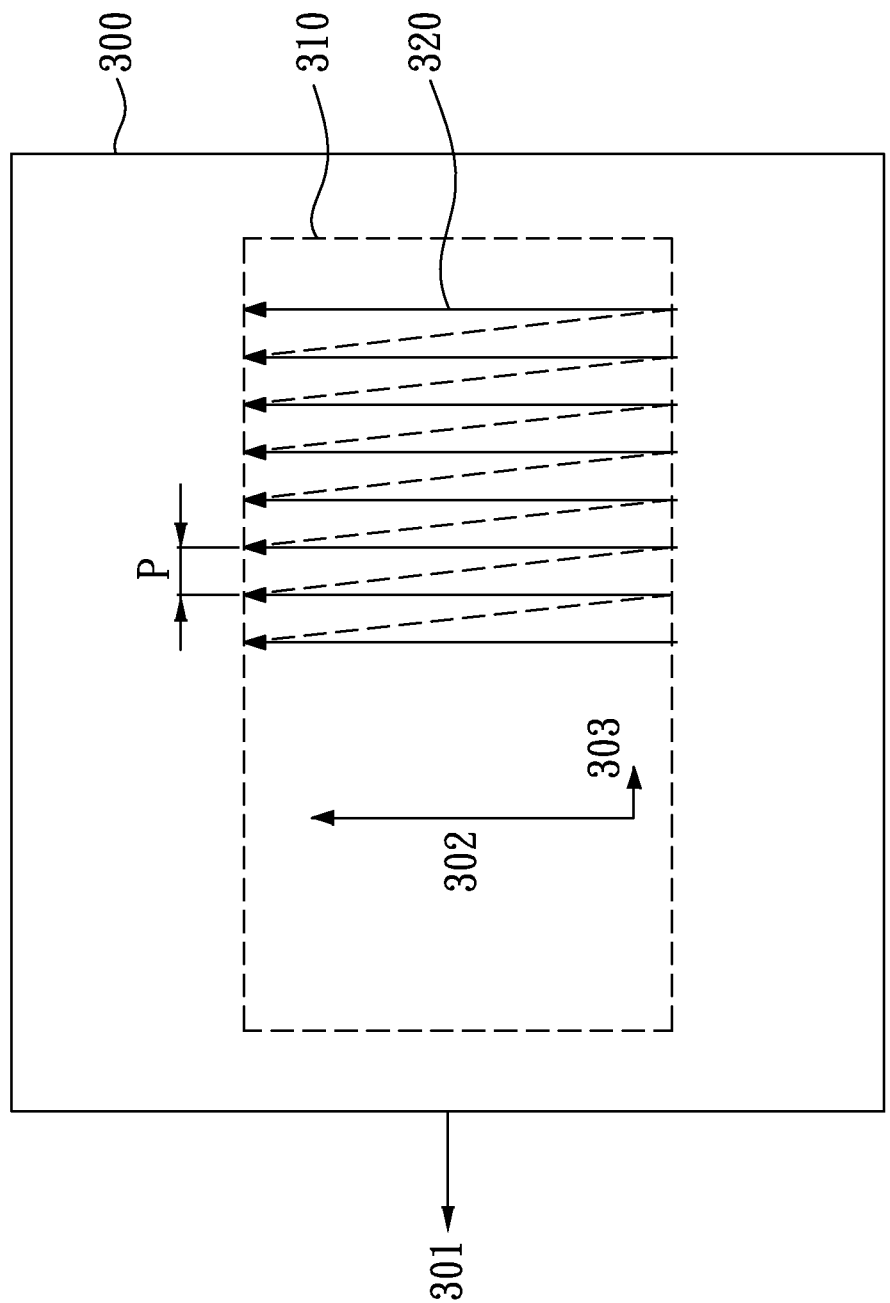
FIG. 3A is a schematic illustration of raster scan in accordance with the conventional art.

Referring to FIG. 3A, a schematic illustration of a raster scan may be likened to that of the conventional art. It is first noted that the continuously moving stage mode is used as an example here to describe the conventional raster scan. This is merely for simplicity of explanation and should not limit the scope of the present invention. As shown, sample 300 is held on a stage moving at a predefined constant speed in a stage moving direction 301. Electron beam, for example, meanwhile is scanned over the surface of sample 300 in two directions such as, typically, a line scan direction 302 and a line-to-line advancement direction 303. In this example, the line scan direction 302 is selected to be substantially perpendicular to the stage moving direction 301 for covering the width of the obtained image while the line-to-line advancement direction 303 is selected to be substantially perpendicular to the line scan direction 302. The net effect of electron beam scan components in line-to-line advancement direction 303 and stage moving direction 301 defines the line-to-line scan offset. A two-dimensional array of scan lines 320 is, thus, accordingly formed on the surface of sample 300. It is noted that the dotted line in scan line array 320 indicates the trace of the scanning beam's flying back from the end of the previous scan line to the start of the next scan line. The distance between each scan line is called the pixel size and is denoted "P."

If the stage moving speed 301 is equal to zero, i.e. sample 300 is held on a stationary stage, then this example is equivalent to a raster scan implemented in the step-and-repeat mode. If the line-to-line advancement component 303 is equal to zero, i.e. the stage is in motion with a constant speed, then this example is equivalent to the typical continuously moving stage mode. In one embodiment of the present invention, neither the stage moving direction 301 nor the line-to-line advancement direction 303 is equal to none, i.e. the sample stage is moving one-dimensionally and the charged particle beam is being raster scanned two-dimensionally during imaging.

Figure 3B:
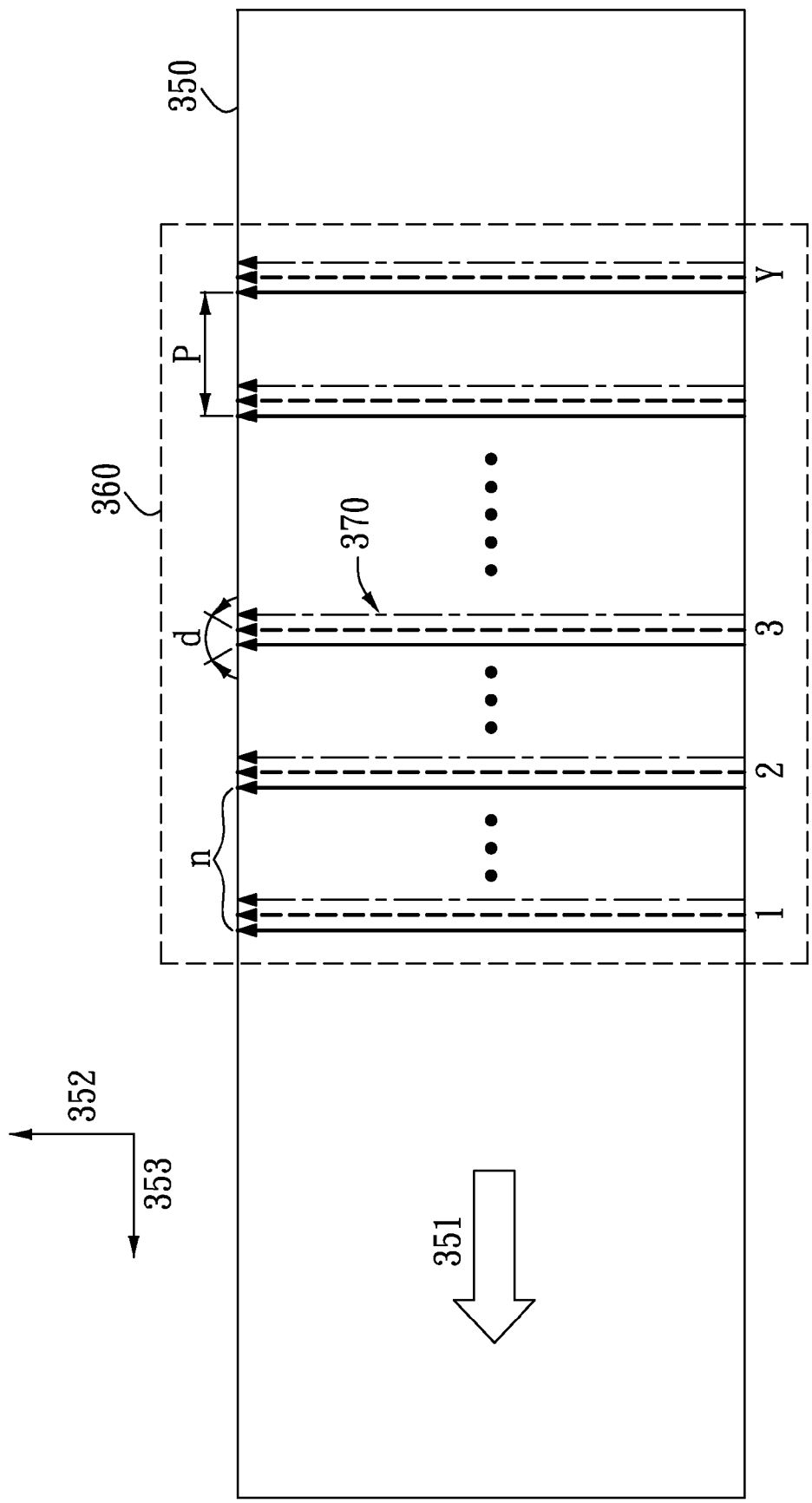
FIG. 3B is a schematic illustration of a charged particle beam imaging method in accordance with an embodiment of the present invention.

As distinguished from the traditional repeated single line scans of FIG. 3A forming a single condition image, the embodiment of FIG. 3B shows a group of n line scans being repeated such that "m" groups of n scan lines are formed on the sample, whereby image(s), each formed at a different imaging condition synchronized with the formation of individual scan lines, are thus obtained. Image signals from collections of m scan lines with each from a corresponding group of n scan lines are used to form at most n images, with each being formed at a different imaging condition. In one example, m is selected as a specific number, n is selected to be an integer greater than or equal to 2, and X and Y are both selected to be an integer greater than 2. If an image size of X*Y pixels with a predefined pixel size p (as shown in FIG. 3B) is desired for an image of a single condition, m can be selected to be Y, and the image size of the newly obtained images is X*Y*n pixels regardless of the number of images ultimately obtained.

It is noted that for such a case, the total n*Y scan lines formed may be spaced apart by a fixed distance d (as shown in FIG. 3B) such that the product of n and d is equal to the specified pixel size p, i.e. n*d=p. Alternatively, the product of n and d may be greater than the specified pixel size p (n*d>p) or less than the specified pixel size p (n*d<p). The later cases, however, may render deformed images.

As shown in FIG. 3B, a sample 350 travels along a sample moving direction indicated as 351. In one example, sample 350 is secured on a stage for imaging, and the sample moving direction 351 is selected to be along the stage moving direction. A charged particle beam is repeatedly line-scanned over an area of interest 360 on sample 350 with a line scan direction 352 and line-to-line advancement direction 353. In one example, sample moving direction 351 is selected to be in the direction identical to line-to-line advancement direction 353. In one example, line-to-line advancement direction 353 is selected to be perpendicular to line scan direction 352. Scanning of the charged particle beam forms a plurality of n*Y scan lines 370 on sample 350 through repeatedly forming a group of n scan lines 370 for Y times on the moving sample 350. It is noted that in this embodiment, the above mentioned "Y" dimension of pixels is measured along the line-to-line advancement direction 353.

The imaging condition at which each scan line 370 is formed may be the same or different. Moreover, the change in imaging conditions is synchronized with each line scan and kept unchanged during the line scan. As shown in FIG. 3B, different line characters of scan line 370 indicate a different imaging condition. In other words, the imaging conditions for the 1st scan line (bold solid line), 2nd scan line (bold dotted line), and the 3rd scan line (thin dotted line), etc. are different from each other.

In one embodiment, the imaging condition change is realized by varying the power of the optical beam(s) (from one or more sources). During the formation of each scan line 370, the optical beam(s) illuminate the area 360 to be scanned by the charged particle beam. The power of the optical beam(s) is modulated to a fixed level prior to or simultaneously with scanning of the charged particle beam on the sample, and kept unchanged during each line scan.

In another embodiment, the imaging condition change is realized by varying the wavelength of optical beam(s) (from one or more sources). During the formation of each scan line 370, the optical beam(s) illuminate the area 360 to be scanned by the charged particle beam. The wavelength of the optical beam(s) is varied prior to or simultaneously with scanning of the charged particle beam on the sample, and kept unchanged during each line scan.

In a more general embodiment, the imaging condition change is realized by varying the wavelength, power or combination thereof for the optical beam(s) (from one or more sources). In one embodiment, the optical beam may be illuminated on the sample in synchronization with (for example, simultaneously with or prior to) scanning of the charged particle beam with a varying or constant beam intensity, wavelength, beam energy, duration of illumination, or any combination thereof.

Figure 3E:
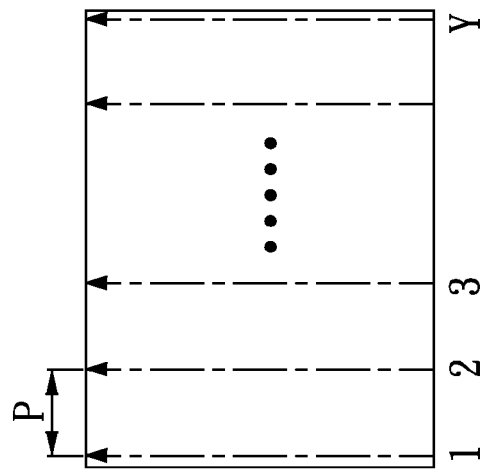
FIG. 3E is a schematic illustration of an image of a sample formed in accordance with an embodiment of the present invention.
Figure 3D:
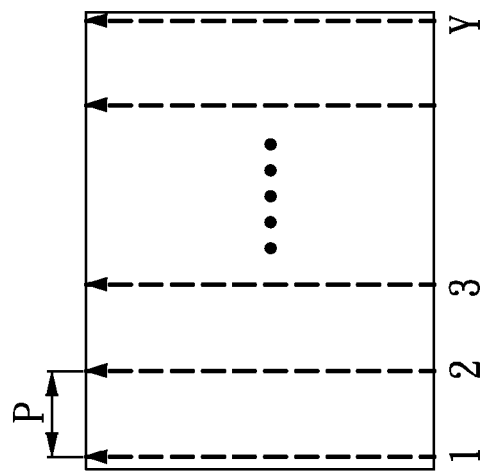
FIG. 3D is a schematic illustration of an image of a sample formed in accordance with an embodiment of the present invention.
Figure 3C:
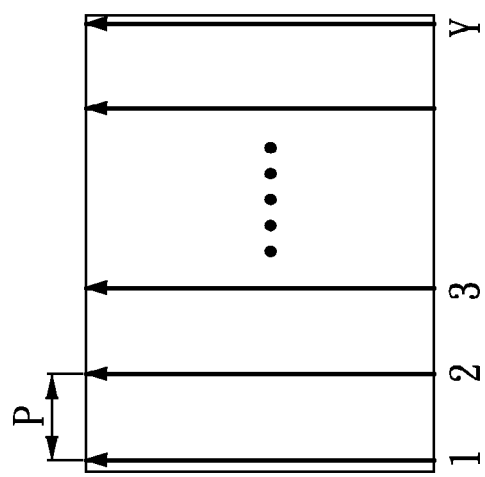
FIG. 3C is a schematic illustration of an image of a sample formed in accordance with an embodiment of the present invention.

In this embodiment, n images are obtained from the n*Y scan lines. The obtained n images are formed at n different imaging conditions, each synchronizing with individual line scans. FIGS. 3C, 3D and 3E, illustrative of such situation, are images of a sample formed in accordance with embodiments of the present invention. As shown, each of the n images is formed from image signals collected from selected Y line scans out of the total n*Y line scans. In other words, scan lines correspondingly selected from each of the Y groups of scan lines are used to form one of the (at most) n images. For example, as shown in FIG. 3C, the 1st scan line (bold solid line) within each of the Y groups of scan lines is selected to provide the image signals for forming a 1st image of area 360. As shown in FIG. 3D, the 2nd scan line (bold dotted line) within each of the Y groups of scan lines is selected to provide the image signals for forming a 2nd image of area 360. As shown in FIG. 3E, the 3rd scan line (thin dotted line) within each of the Y groups of scan lines is selected to provide the image signals for forming a 3rd image of area 360, and so on and so forth. It is noted from FIGS. 3C, 3D and 3E that each formed image has Y pixels with a pixel size p along the line-to-line advancement direction. Further, each formed image covers substantially the same physical area 360 on sample 350.

Figure 3F:
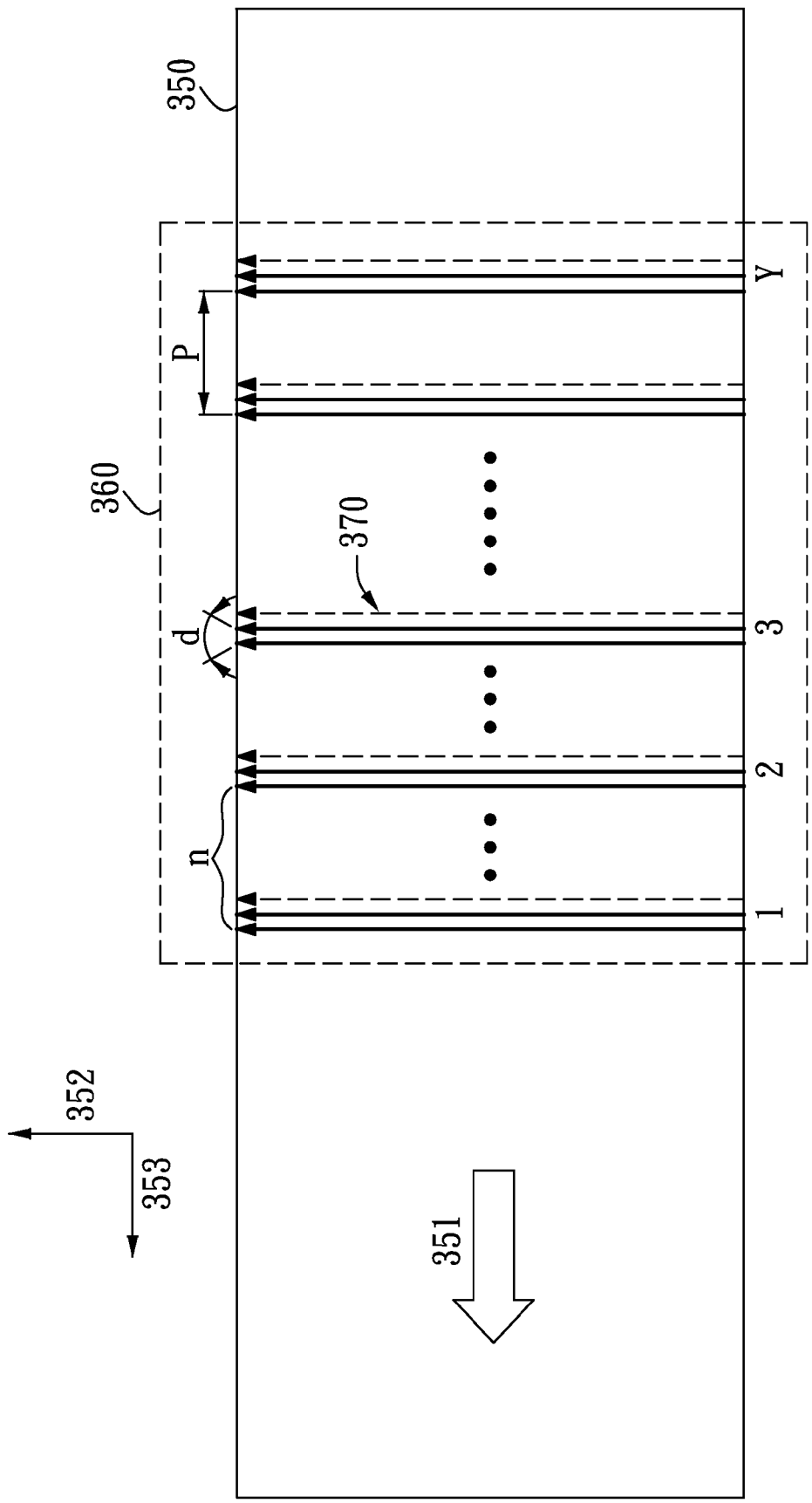
FIG. 3F is a schematic illustration of a charged particle beam imaging method in accordance with an embodiment of the present invention.

However, as mentioned earlier, the image signals from the n*Y scan lines (in Y groups of n scan lines) may be used for forming "at most" n images. This is because not each scan line needs to be set to be formed at a different imaging condition. For example, multiple scan lines may be set to be formed at the same imaging condition, and then the image signals from these scan lines are averaged to give an enhanced image quality. In such case, the total number of images that may be obtained from the n*Y scan lines must be less than n. FIG. 3F is a schematic illustration of a charged particle beam inspection method in accordance with an embodiment of the present invention. As this embodiment is similar to that of FIG. 3B, descriptions of similar elements and associated notations will not be repeated here. As shown, the 1st and 2nd scan lines in each of the Y groups of scan lines are represented in an identical bold line. This means that the 1st and 2nd scan lines are formed at the same imaging condition. Therefore, image signals from these two scan lines can be averaged to form one image with enhanced quality. As a result, the total images that will be obtained from n*Y scan lines is (n-1) in this embodiment. In accordance with one exemplary implementation, image signals from scan lines formed at different imaging conditions may be averaged as well.

It is noted that the embodiment of FIG. 3B, by changing the imaging condition in a substantially line-by-line manner, allows for the optical illumination-assisted charged particle beam inspection to be realized in one inspection action. In other words, the need to repeat imaging at different imaging conditions (e.g. illumination ON vs. OFF) is eliminated. For example, for such inspection to be performed in the continuously moving stage mode, the stage does not need to move back and forth. Multiple images targeting at the inspection of different types of defects can be produced as the stage moves along. This greatly improves the inspection throughput.

Figure 3G:
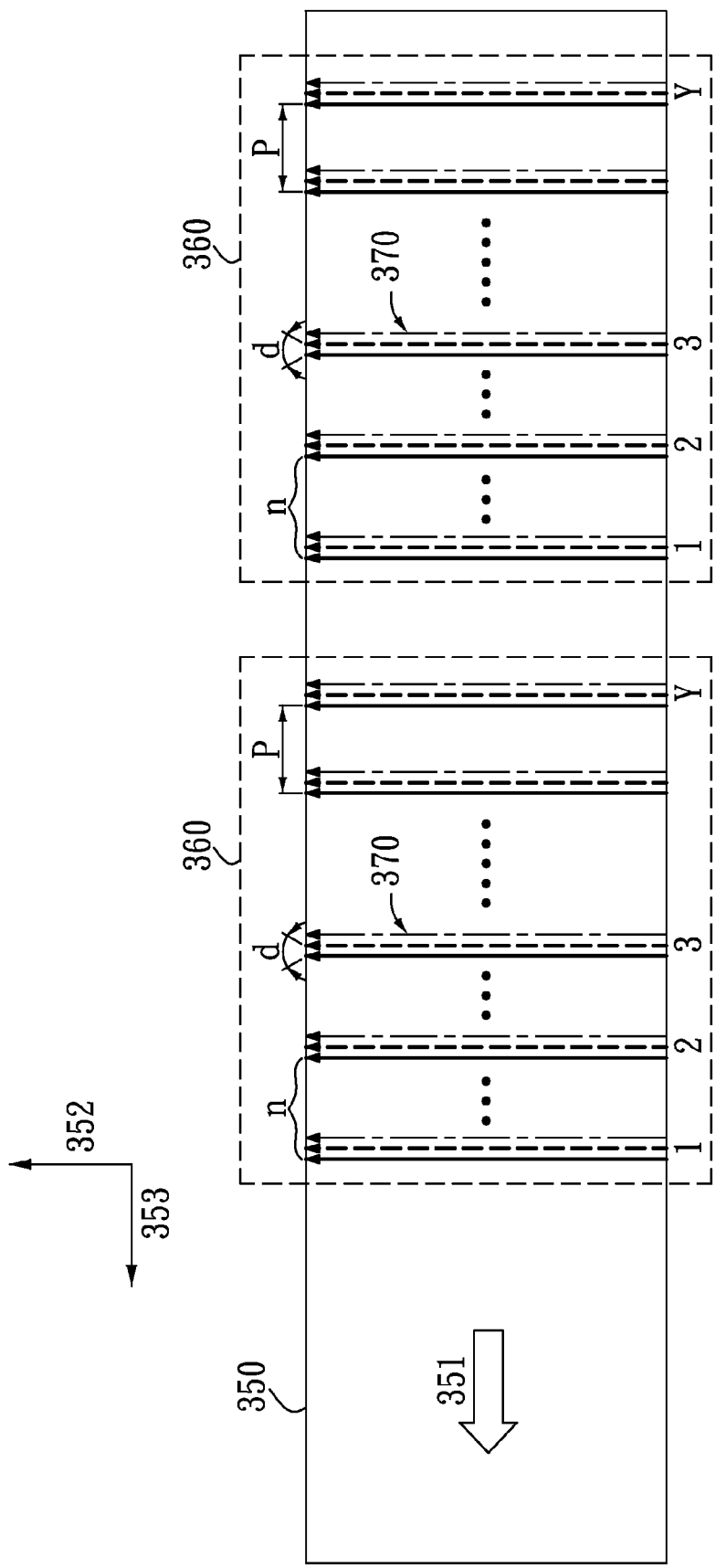
FIG. 3G is a schematic illustration of a prolonged version of the disclosed imaging method illustrated in FIG. 3B in accordance with an embodiment of the present invention.

As mentioned earlier, the patterns in the imaged area of interest may be represented in grey level profiles in the obtained images. Defects existing in the imaged patterns may be identified from these grey level images as abnormal grey levels or abnormal VCs. In one example, individual obtained images may be inspected independently. For instance, if the patterns in the area of interest are formed in repetition, defect identification can be performed by analyzing the grey level profiles displayed by the repeating patterns in the concerned image. Alternatively, cross-image comparison may be used. FIG. 3G is a schematic illustration of a prolonged version of the disclosed imaging method illustrated in FIG. 3B in accordance with an embodiment of the present invention. It is noted first that similar elements and notations which have been described in conjunction with FIG. 3B will not be repeated here. In this embodiment, the disclosed imaging method is performed to image a moving sample 350 which has multiple areas 360 thereon. In one example, these areas 360 have identical patterns and layouts, and may be located at a corresponding location(s) on different dies and/or sides. As shown in FIG. 3G, when sample 350 continues to move forward along direction 351, the disclosed imaging method is repeatedly performed such that two or more separate areas 360 are imaged at identical imaging conditions. Assume n images are produced per imaging of area 360, then two or more sets of n images (each representing one area 360) will be obtained. Next, images formed at the same imaging condition, i.e. images formed from image signals generated by line scans performed at the same imaging condition, can be compared against each other to detect the presence of defects in the concerned image. For example, in FIG. 3G, images formed by image signals collected from 1st scan lines for each of the two imaging areas 360 may be compared.

In another example, some or all of the obtained images can first be combined through mathematical operation such as linear addition, subtraction, etc., such that noises and/or grey levels of normal patterns are canceled or suppressed, and/or the grey level contrast between the normal and defective patterns are enhanced, making the inspection easier. Examples of the mathematical operations are linear addition, subtraction, etc. These operations are common image processing techniques, and details thereof will not be repeated here. In a further example, the individual images are compared against each other. As would be understood by those skilled in the art, combinations of the above image inspection methods are also possible for the ultimate purpose of identifying defects from the obtained grey level images.

In one embodiment, the disclosed method is applied for the inspection of a sample having both NMOS and PMOS devices thereon, such as an SRAM. In another embodiment, the disclosed method can be applied for the inspection of photo diodes, CMOS sensors, and/or other devices that are sensitive to optical beam illumination.

Figure 4B:
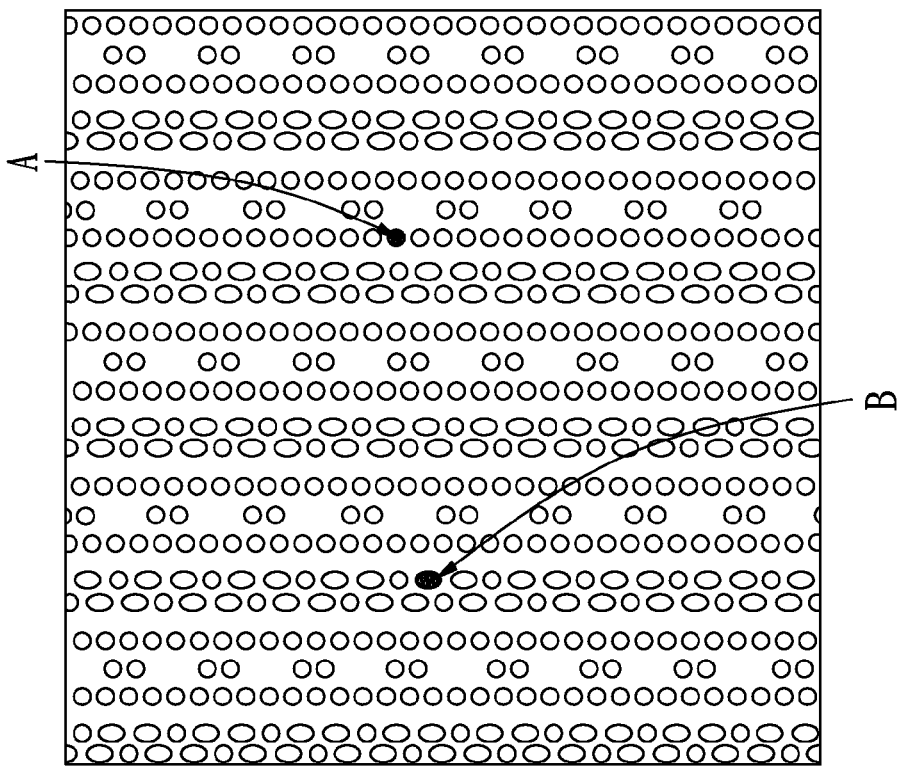
FIG. 4B is a schematic illustration of a positive imaging mode VC image captured with laser beam illumination of the SRAM device illustrated in FIG. 4A in accordance with an embodiment of the present invention.
Figure 4A:
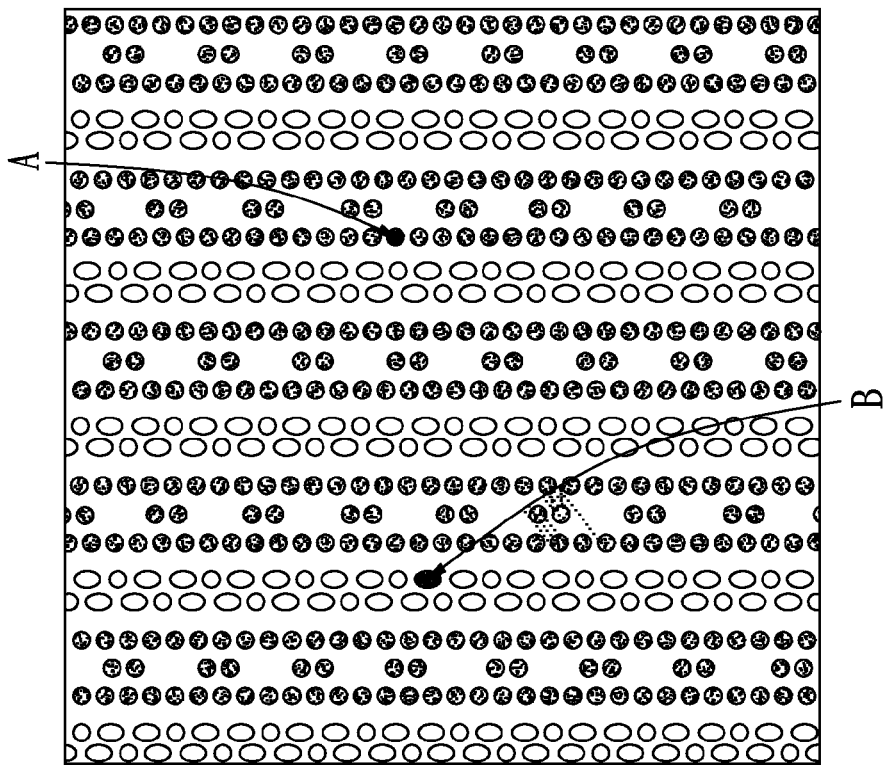
FIG. 4A is a schematic illustration of a positive imaging mode VC image of an SRAM device captured without laser beam illumination in accordance with an embodiment of the present invention.

With reference to FIG. 4A, a schematic is provided of a positive imaging mode VC image of an SRAM device captured without laser beam illumination in accordance with an embodiment of the present invention. Plugs connected to N+/P-wells appear relatively dark as associated junctions are reverse biased, while plugs connected to P+/N-wells appear bright as forward biasing occurring thereto helps in the release of positive charging on the device surface. As shown in FIG. 4A, two abnormal contacts are indicated as A and B, respectively. Contact A is an open plug landing on an N+/P-well, appearing slightly darker than normal ones, while contact B is an open plug landing on a P+/N-well, appearing dark in contrast with the bright normal ones. It may be difficult to maintain balanced detection sensitivity for these two types of open plugs.

Referring to FIG. 4B, another schematic is provided this time of a positive imaging mode VC image captured with laser beam illumination of the SRAM device of FIG. 4A in accordance with an embodiment of the present invention. In one example, the laser beam is selected to have a power of 5mW and a wavelength of 650nm. Alternatively, or additionally, power and wavelength may be used according to other examples. If the area is illuminated by an optical beam when being imaged with an EBI apparatus, normal N+plugs will gradually turn from dark to bright as the illumination power increases, finally reaching a state where all N+plugs appear as bright as that of P+plugs. The abnormal plugs coupled to the open contact, however, are not affected by illumination of the laser beam. This may make the two abnormal plugs A and B drop in the grey level up to 50% when compared to their normal counterparts. As a result, balanced detection sensitivity for open defects on both P+/N-well (defect B) and N+/P-well (defect A) can be achieved, as shown in FIG. 4B.

Figure 5B:
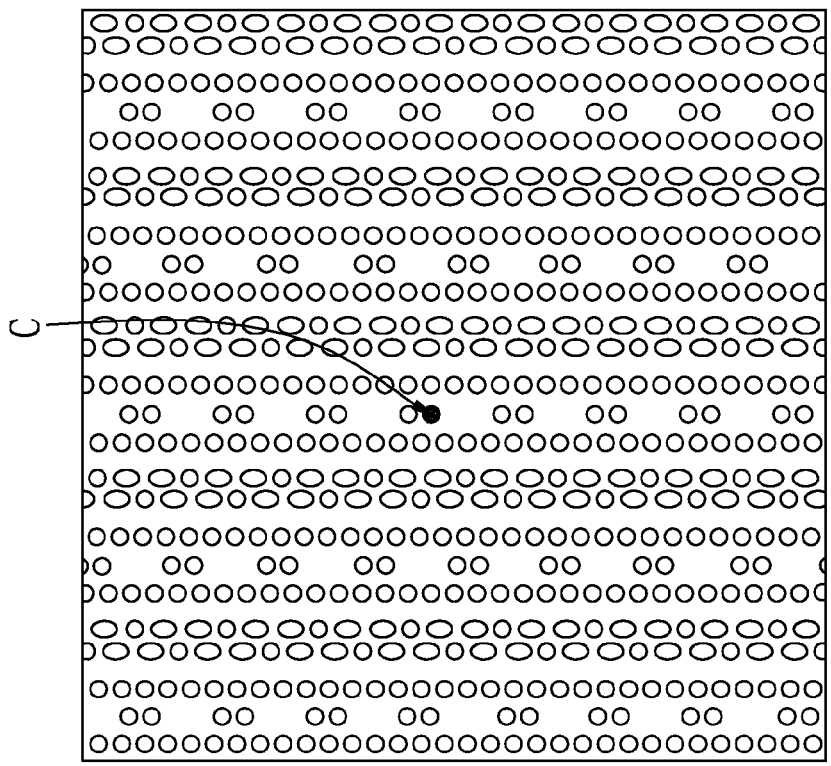
FIG. 5B is a schematic illustration of a positive imaging mode VC image captured with laser beam illumination of the SRAM device illustrated in FIG. 5A in accordance with an embodiment of the present invention.
Figure 5A:
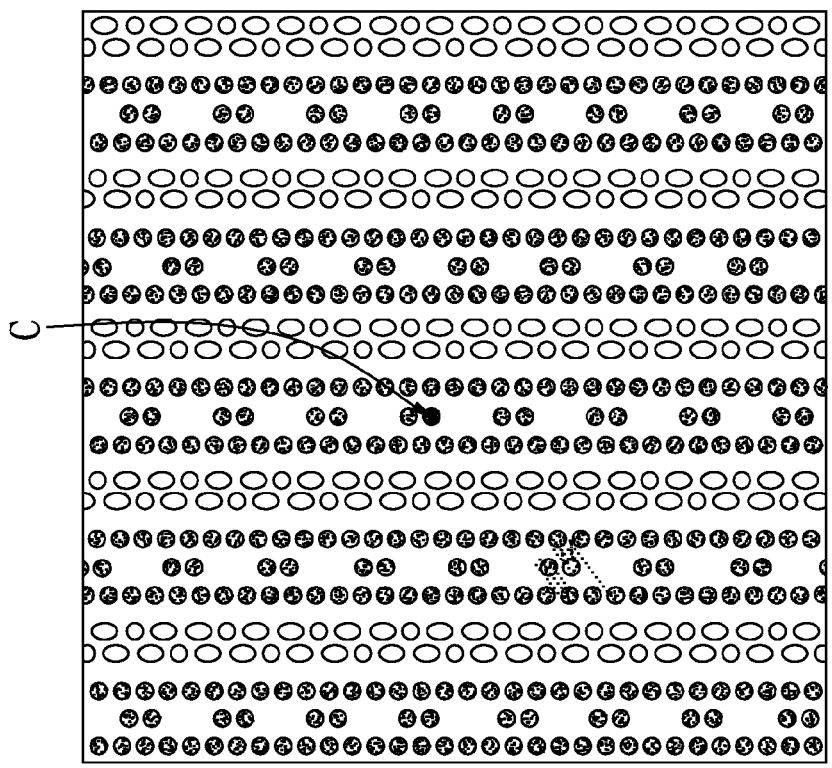
FIG. 5A is a schematic illustration of a positive imaging mode VC image of an SRAM device captured without laser illumination in accordance with another embodiment of the present invention.

Another example effect of laser beam illumination is that it boosts gate leakage thus revealing gate contact open conditions. Referring to FIG. 5A, which is a schematic illustration of a positive imaging mode VC image of an SRAM device captured without laser illumination in accordance with an embodiment of the present invention, normal gate plugs appear dark due to positive charging accumulation which is difficult to be released to the substrate via the gate oxide. The abnormal open gate contact shows up slightly darker, as indicated by arrow C. The difference in grey level due to the contact open condition may be about 30% as compared to the normal. Referring to FIG. 5B, which is a schematic illustration of a positive imaging mode VC image captured with laser beam illumination of the SRAM device of FIG. 5A in accordance with an embodiment of the present invention, when the laser is on, the laser light more or less stimulates gate oxide leakage and draws away excess positive charges on the normal gate. The normal gate plugs are thus lit up. On the contrary, the open gate plug is almost not affected by illumination of the laser beam. A measurement shows that the open gate plug grey level may drop in grey level up to 50% from the normal.

Figure 6:
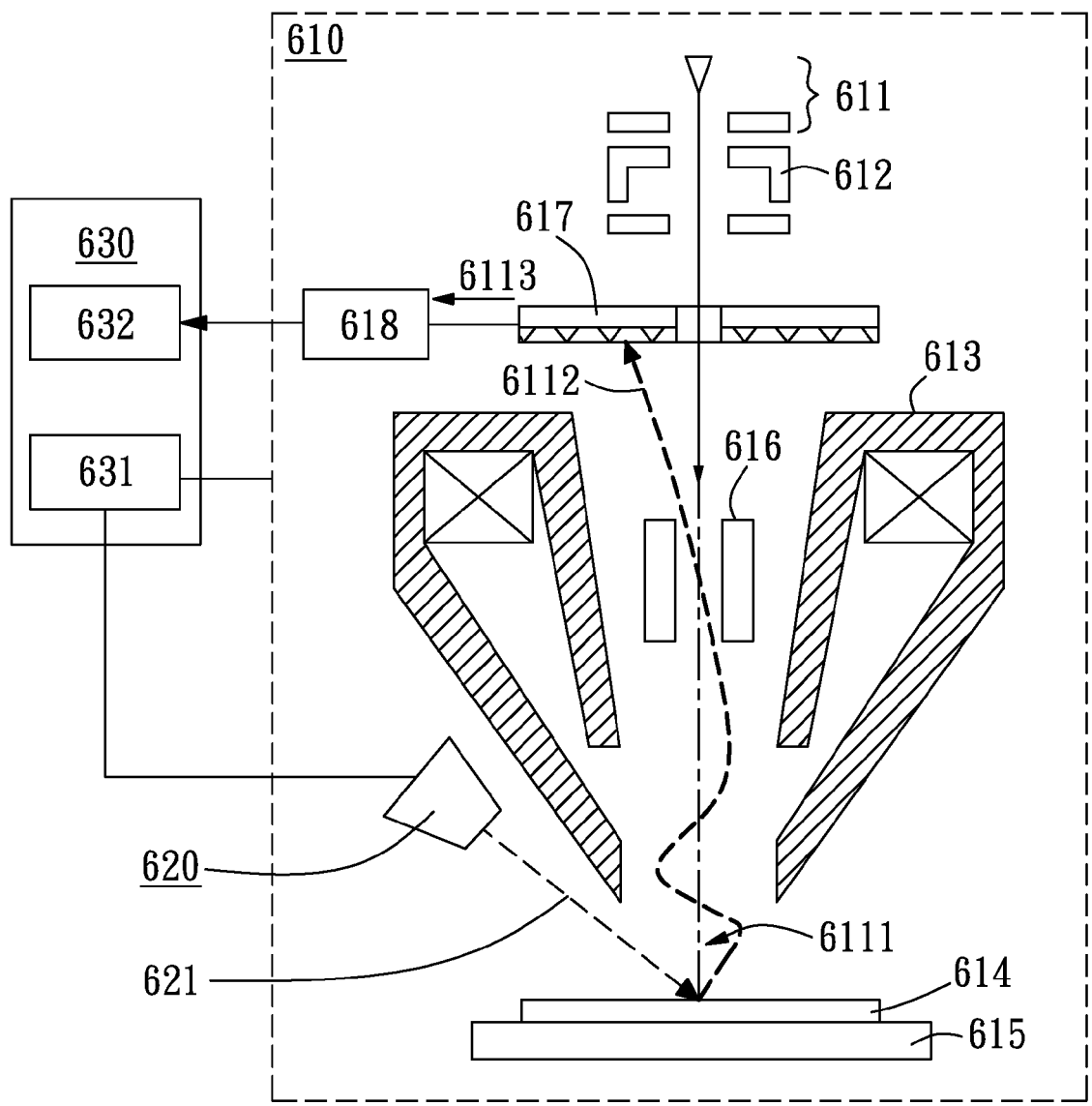
FIG. 6 is a schematic illustration of a charged particle beam inspection system in accordance with an embodiment of the present invention.

In one embodiment, a charged particle beam inspection system is disclosed. Referring to FIG. 6, which is a schematic illustration of a charged particle beam inspection system in accordance with an embodiment of the present invention, a charged particle beam inspection system 600 comprises a charged particle beam imaging apparatus 610, an optical beam apparatus 620, and a defect determination apparatus 630. Charged particle beam imaging apparatus 610 is for forming a grey level or voltage contrast image of a sample of interest. Optical beam apparatus 620 is for illuminating an optical beam on the sample. Defect determination apparatus 630 comprises a control module 631 and an image analysis module 632.

Charged particle beam imaging apparatus 610 may be a conventional charged particle beam microscope, such as a scanning electron microscope (SEM). As shown in FIG. 6, in charged particle beam imaging apparatus 610, a charged particle beam generator 611 generates a charged particle beam, and then the charged particle beam is condensed and focused by a condenser lens module 612 and an objective lens module 613, respectively, to form a charged particle beam probe 6111. The formed charged particle beam probe 6111 then bombards the surface of a sample 614 secured on a sample stage 615. Charged particle beam probe 6111 is controlled by a deflection module 616 to scan the surface of sample 614. After charged particle beam probe 6111 bombards the surface of sample 614, secondary charged particles 6112 are induced to be emitted from the sample surface along with other charged particles of beam probe 6111 reflected by sample 614. These particles are then detected and collected by a detector module 617. Then, detector module 617 generates a detection signal 6113 accordingly. An image forming module 618 coupled to detector module 617 receives detection signal 6113 and accordingly forms a charged particle microscopic image (grey level image) of sample 614.

Control module 631 is coupled to charged particle beam imaging apparatus 610 and optical beam apparatus 620 for controlling these elements such that when sample 614 is being imaged, an optical beam 621 is selectively illuminated on sample 614 in coordination with the scanning of the imaging charged particle beam probe 6111. In particular, charged particle beam probe 6111 is line-scanned over the surface of sample 614 to form a plurality of n*Y scan lines by repeatedly forming a group of n scan lines for Y times. In addition, during the formation of each group of n scan lines, optical beam 621 is, from one line scan to another, selectively illuminated on the surface of sample 614 prior to or simultaneously with scanning of the charged particle beam probe 6111. Moreover, during the formation of each group of n scan lines, a condition of illumination of optical beam 621 selectively changes from one line scan to another. The conditions at which individual n scan lines are formed may be repeated for the formation of all Y groups of scan lines.

In one example, control module 631 is coupled to deflection module 616 to control the scanning of charged particle beam probe 6111 over sample 614. In another example, control module 631 is coupled to deflection module 616 and/or sample stage 615 to control the relative motion of charged particle beam probe 6111 and sample 614, so as to carry out the line-to-line advancement of the scanning charged particle beam probe 6111. In a further example, sample stage 615 is controlled by control module 631 to move sample 614 continuously along the line-to-line advancement direction of the scanning charged particle beam probe 6111, such that the charged particle beam imaging is performed in the continuous scan mode.

Image analysis module 632 is coupled to charged particle beam imaging apparatus 610 for receiving the grey level/voltage contrast image of sample 614 therefrom. In one example, image analysis module 632 is coupled to image forming module 618.

With optical beam illumination controlled to be selectively performed in coordination with scanning of charged particle beam probe 6111, charged particle beam inspection system 600 is able to carry out the defect inspection method for the sample 614 as disclosed in embodiments of FIGS. 3 to 5. For example, defects identified from images formed with and without illumination of optical beam 621 on sample 614 are compared against each other so as to determine the presence of certain types of defects on sample 614.

Although the present invention has been explained in relation to its preferred embodiment, it is to be understood that other modifications and variation can be made without departing from the spirit and scope of the invention as hereafter claimed.

What is claimed is:

1. A method for forming a plurality of images on a sample for categorizing defects on said sample, wherein said sample comprises a first pixel column and a second pixel column comprising:
    moving said sample continuously in a direction perpendicular to said first pixel column and said second pixel column, and from said first pixel column to said second pixel column;
    line-scanning said first pixel column with a charged particle beam under a first photo-current condition;
    line-scanning said first pixel column again with said charged particle beam under a second photo-current condition, wherein said second photo-current condition is different from said first photo-current condition;
    line-scanning said second pixel column with said charged particle beam under said first photo-current condition; and
    line-scanning said second pixel column again with said charged particle beam under said second photo-current condition;
    wherein said sample is moved continuously at a speed allowing scanning processing to be done on each pixel column under different photo-current conditions.

2. The method of claim 1, wherein said condition of illumination of said optical beam remains constant during one line scan.

3. The method of claim 1, wherein said condition of illumination of said optical beam includes optical beam intensity, optical beam wavelength, optical beam energy, duration of illumination, or any combination thereof.

4. The method of claim 1, wherein during the formation of each said group of n scan lines, at least two scan lines are formed at identical said condition of illumination of said optical beam.

5. The method of claim 1, wherein said n*Y scan lines are spaced apart by a fixed distance d such that the product of n multiplied by d is equal to said predefined pixel size p (n*d=p).

6. The method of claim 1, wherein said charged particle beam is offset by one or more lines along the line-to-line advancement direction.

7. The method of claim 1, wherein each of formed said images is inspected independently.

8. The method of claim 1, wherein formed said images are inspected collectively after being combined through mathematical operation.

9. The method of claim 1, wherein each said image is formed from a collection of Y said scan lines correspondingly selected from each of said Y groups of n scan lines.

10. The method of claim 1, wherein said predefined types of defects comprise the N+/P-well plug open defect, the P+/N-well plug open defect, N+/P-well plug leakage defect, P+/N-well plug leakage or any combination thereof.

11. The method of claim 1, wherein illumination of said optical beam causes patterns of particular material or electrical properties in said area to display a brighter grey level.

12. The method of claim 1, wherein X, Y and n are an integer equal to or greater than 2.

13. The method of claim 1, wherein said condition of illumination of said optical beam is modulated on/off or to different power levels or selected from different sources of wavelength, in synchronization with said line-scanning.

14. A charged particle beam inspection system for categorizing defects on a sample with a first pixel column and a second pixel column, comprising:
  a charged particle beam imaging apparatus for forming voltage contrast images of said sample by scanning a charged particle beam over said first pixel column and said second pixel column;
  an optical beam apparatus for illuminating said sample to induce a first photo-current condition and a second photo-current condition on said sample, wherein said first photo-current condition is different from said second photo-current condition; and
  a defect determination apparatus comprising a control module and an image analysis module, wherein said control module is coupled to and controls said charged particle beam imaging apparatus and said optical beam apparatus
  wherein said charged particle beam imaging apparatus scans said first pixel column under said first photo-current condition, then scans said first pixel column under said second photo-current condition, then scans said second pixel column under said first photo-current condition, and then scans said second pixel column under said second photo-current condition; and
  wherein said sample is moved continuously at a speed allowing scanning processing to be done on each pixel column under different photo-current conditions and said image analysis module is coupled with said charged particle beam imaging apparatus for receiving and analyzing said voltage contrast images from said charged particle beam imaging apparatus for categorizing types of defects on said sample.

15. The charged particle beam inspection system of claim 14, wherein said condition of illumination of said optical beam remains constant during one line scan.

16. The charged particle beam inspection system of claim 14, wherein during the formation of each said group of n scan lines, at least two scan lines are formed at identical said condition of illumination of said optical beam.

17. The charged particle beam inspection system of claim 14, wherein said n*Y scan lines are spaced apart by a fixed distance d such that the product of n and d is equal to said predefined pixel size p (n*d=p).

18. The charged particle beam inspection system of claim 14, wherein each said image is formed from a collection of Y said scan lines correspondingly selected from each of said Y groups of n scan lines.

19. The charged particle beam inspection system of claim 14, wherein said charged particle beam imaging apparatus comprises:
  a charged particle beam generator for generating a charged particle beam;
  a condenser lens module for condensing the generated said charged particle beam;
  an objective lens module for focusing the condensed said charged particle beam into a charged particle beam probe;
  a deflection module for scanning said charged particle beam probe over the surface of said sample secured on a sample stage;
  a detector module for collecting charged particles coming from said sample when it is scanned by said charged particle beam probe, and generating a detection signal accordingly; and
  an image forming module coupled to said detector module for receiving said detection signal and accordingly forming said voltage contrast images of said sample.

* * * * *